(12) United States Patent
Abhari et al.

(10) Patent No.: US 11,628,233 B1
(45) Date of Patent: Apr. 18, 2023

(54) SURFACE SANITIZING DEVICE

(71) Applicant: Ultralizer Inc., Hamilton (CA)

(72) Inventors: Bijan Abhari, Michigan, MI (US); Yadollah Shakiba, Tehran (IR); Gita Shayegan Pour, Toronto (CA); Ghasem Amrollahi Bouoki, Tehran (IR); Mehdi Sanjari, Burlington (CA)

( * ) Notice: Subject to any disclaimer, the term of this patent is extended or adjusted under 35 U.S.C. 154(b) by 0 days.

(21) Appl. No.: 17/849,230

(22) Filed: Jun. 24, 2022

(51) Int. Cl.
| | |
|---|---|
| *A61L 2/10* | (2006.01) |
| *A61L 2/22* | (2006.01) |
| *A61L 2/18* | (2006.01) |
| *A61L 2/24* | (2006.01) |

(52) U.S. Cl.
CPC ........ *A61L 2/10* (2013.01); *A61L 2/18* (2013.01); *A61L 2/22* (2013.01); *A61L 2/24* (2013.01); *A61L 2202/11* (2013.01); *A61L 2202/122* (2013.01); *A61L 2202/14* (2013.01); *A61L 2202/15* (2013.01)

(58) Field of Classification Search
CPC ...... A61L 2/10; A61L 2/18; A61L 2/22; A61L 2/24; A61L 2202/11; A61L 2202/122; A61L 2202/14; A61L 2202/15
See application file for complete search history.

(56) References Cited

U.S. PATENT DOCUMENTS 9,107,973 B1 * 8/2015 Robinson .................. A61L 2/10

* cited by examiner

*Primary Examiner* — Sean E Conley
(74) *Attorney, Agent, or Firm* — Nasser Ashgriz; UIPatent Inc.

(57) ABSTRACT

The present invention is a sanitizing and disinfecting device that provides a long-term sanitizing solution. The device provides a UV-C light for disinfecting objects and provides a thin antimicrobial coating which has UV curable properties to create a long-lasting sanitizing effect. The device comprises a chamber containing UV-C lamps and necessary parts to facilitate spray coating application. A self-elevating system positions the object in an appropriate height for a proper spraying.

9 Claims, 9 Drawing Sheets

SURFACE SANITIZING DEVICE

FIELD OF THE INVENTION

The present invention relates in general to systems and methods for ultraviolet (UV) disinfection, sterilization and sanitization and in specific to a surface sanitizer, and an effective and long-term sanitizing solution that relies both on the UV-C sanitizing and thin antimicrobial coating.

BACKGROUND OF THE INVENTION

Infections can be transmitted through devices like mobile phones, computer keyboards, and many other derives that are commonly used by us. Many infectious agents can survive for extended periods unless they are eliminated by disinfection or sterilization procedures.

High-touch surfaces are one of the potential sources of pathogenic transmission, and they can increase the risk of infections. Touch objects act as important origins of hospital-acquired infection (HAI), as 80% of infections are spread through hand contact. CDC estimates that just in the USA, more than 1M HAI causes 100k deaths per year. For examples, mobile phones, which are in contact with face, lips and ears, are sources of infection paths. Using disinfectant wipes once daily for mobile phones and keyboards can decrease the probability of contamination and spreading of bacterial pathogens through these devices. However, most keyboards have over 101 individual keys, which makes it difficult to disinfect thoroughly. Therefore, the opportunity for the transmission of contaminating microorganisms by these devices is high.

Sanitizing and disinfecting everyday use objects can drastically reduce the amount of life lost due to HAI. The currently available disinfection products provide a one-time disinfection at the time of application. They keep the object vulnerable to bacterial attachment and consequent growth immediately after disinfection.

One of the most effective and accessible solution for sanitizing and disinfection an everyday item is a UV light. For hard surfaces, UV disinfection is superior to chemical disinfection in terms of environmental footprint, operating costs as well as ease of operation. UV disinfection technology is well-established and well-understood. It is uncomplicated and straightforward in its operating principle.

UV light is separated into 3 distinct categories: UV-A (315-400 nm), UV-B (280-315 nm), and UV-C (200-280 nm). Since DNA optimally absorbs UV light at 253.7 nm, it is UV-C lamps that are used in most prior art germicidal devices. It has been well known that ultraviolet (UV) light has germicidal properties by damaging the genetic material of the microorganisms. The inactivation of specific genes is one of the mechanisms of how UV-induced genetic damage can lead to cell death or to the inhibition of cell replication.

UV radiation is used for disinfection in hospitals, nurseries, operating rooms, cafeterias and to sterilize vaccines, serums, toxins, municipal waste, and drinking waters. However, one has to repeatedly apply a UV system on an object throughout a day to keep it sanitized.

Various materials, such as Chlorine disinfectants, are also used for disinfecting hospital wastewater in order to prevent the spread of pathogenic microorganisms, causal agents of nosocomial infectious diseases. These materials are toxic for aquatic organisms and are persistent in environmental contaminants. Other disinfectants, such as sodium hydroxide and citric acid, also have numerous harmful effects.

Other methods currently used for sterilizing fermentation vessels (made from metals and/or wood) include the use of ozone for general surface sanitation. Results have shown the same degree of sanitization as that achieved using caustic for a fraction of the cost and wasted water. Ozone is an unstable gas and readily reacts with organic substances. It sanitizes by interacting with microbial membranes and denaturation metabolic enzymes. Ozone is known to have adverse physiological effects on humans. Even low concentrations of ozone produce transient irritation of the lungs as well as headaches. Higher concentrations induce severe eye and upper respiratory tract irritation.

The present invention is a novel method and system of the sanitation that lasts for long time to prevent the spread of infectious diseases.

SUMMARY OF THE INVENTION

The present invention is a sanitizing and disinfecting device that provides a long-term sanitizing solution. The present invention uses UV-C light to disinfect objects and coats the object with a thin layer of antimicrobial coating. This coating is sprayed onto the object and is cured through the UV process to protect the item from further microbial growth.

The device provides a UV-C light and a thin antimicrobial coating that cures with the UV-C light to provide a long-lasting sanitizing effect. The device comprises a chamber containing UV-C lamps and a mechanism to facilitate spray coating application, and an antimicrobial liquid coating that is UV curable. The chamber comprises of a three-dimensional, 3D, traverse system, a spraying system, a sensor system, and a UV application system. The system is configured to provide a substantially uniform coating on a wide variety of surfaces with different topological configurations.

After the objects are placed inside the device, the sanitization process is done in the following steps. The UV-C lamps is turned on for a pre-programmed period of time. The device is automatically turned off after the set time, and a spraying system is activated. The spray system comprises of a narrow spray angle spray that covers only a small portion of the surface of the object. The sensor system determines the distance between the surface of the object and the nozzle. The 3D platform adjusts the distance between the object surface and the spray nozzle to keep it at a predefined distance. The platform moves the object while the spray nozzle operates, keeping the distance always at the predefined distance. This assures that the whole surface of the item is coated with a constant coating layer. By having a uniform coating thickness, the UV exposure time can be minimized to the time needed to cure the predefined coating thickness. If the coating thickness changes over the surface of the object, the UV exposure time has to be long enough to cure the thickest layer of the coating.

It is an object of the present invention to provide a device that not only sanitizes and disinfects an item but also protects the item in between the sanitizing sessions (i.e., during uses and idling periods) and provides a long-lasting sanitizing effect. One of the major issues with the current UV systems is that they only disinfect the surface, without any lasting effect. As soon as the surface is touched again, bacterial and infectious material can remain on the surface that was disinfected by UV light a second before.

It is another object of the present invention to provide a minimum UV application to sanitize every day-use items and provide a long-term antimicrobial effect. The presently provided thin antimicrobial coating protects the everyday items from bacterial growth in-between sanitizing. This ensures proper long-term disinfection and reduces the chance of pathogenic transmission. The coating itself does not change the aesthetic or functions of the objects. The coating further provides an additional layer of protection from scratch, dust, smudge and weather as the coating is hydrophobic (anti-wetting) in nature.

BRIEF DESCRIPTION OF THE DRAWINGS

Embodiments herein will hereinafter be described in conjunction with the appended drawings provided to illustrate and not to limit the scope of the claims, wherein like designations denote like elements, and in which:

DETAILED DESCRIPTION OF PREFERRED EMBODIMENTS

Figure 1:
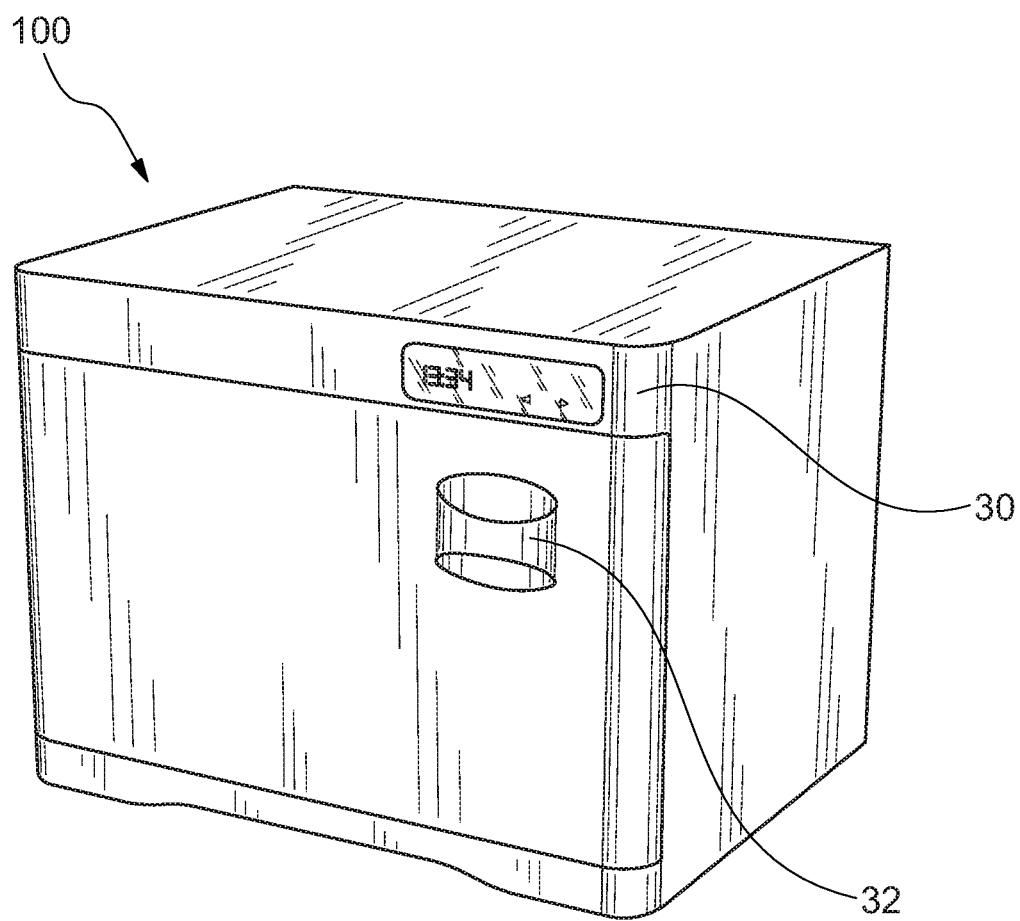
FIG. 1 is a perspective front view of the sanitizing and disinfecting device according to one embodiment of the present invention.
Figure 2:
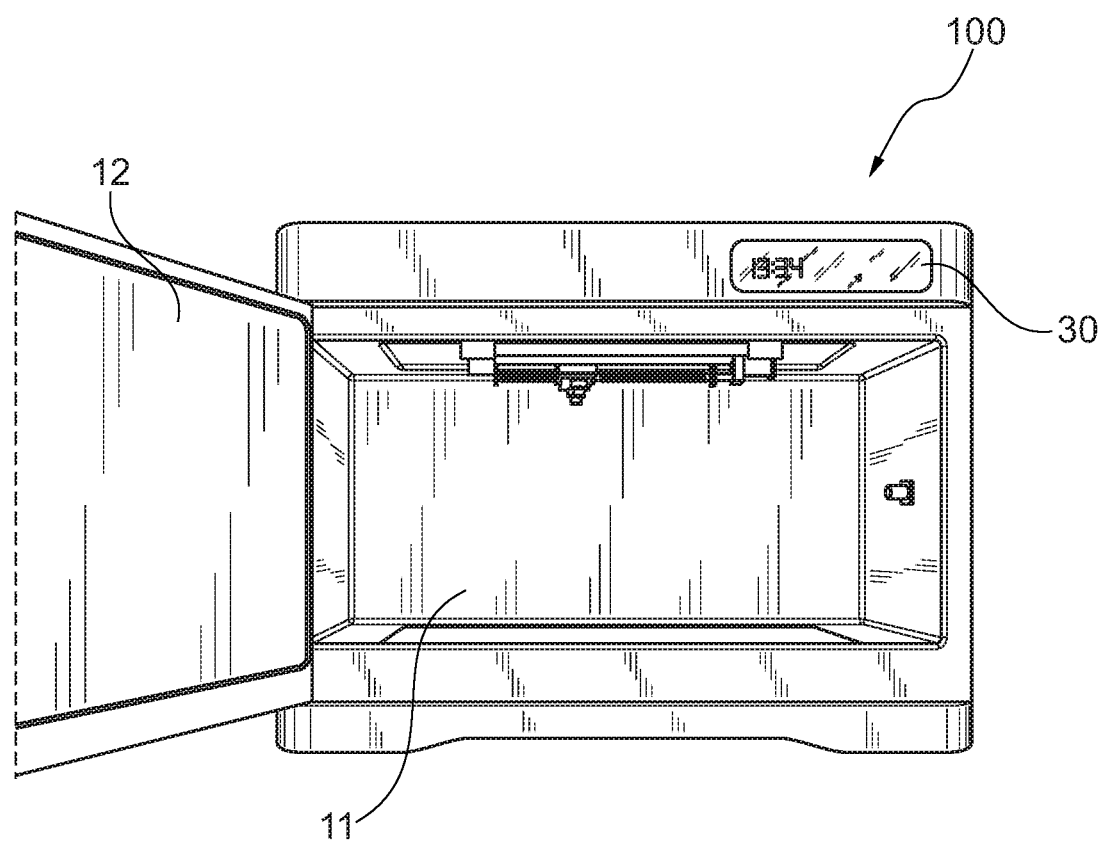
FIG. 2 is a perspective front view of the sanitizing and disinfecting device showing the sanitizing and disinfecting environment according to one embodiment of the present invention.
Figure 3:
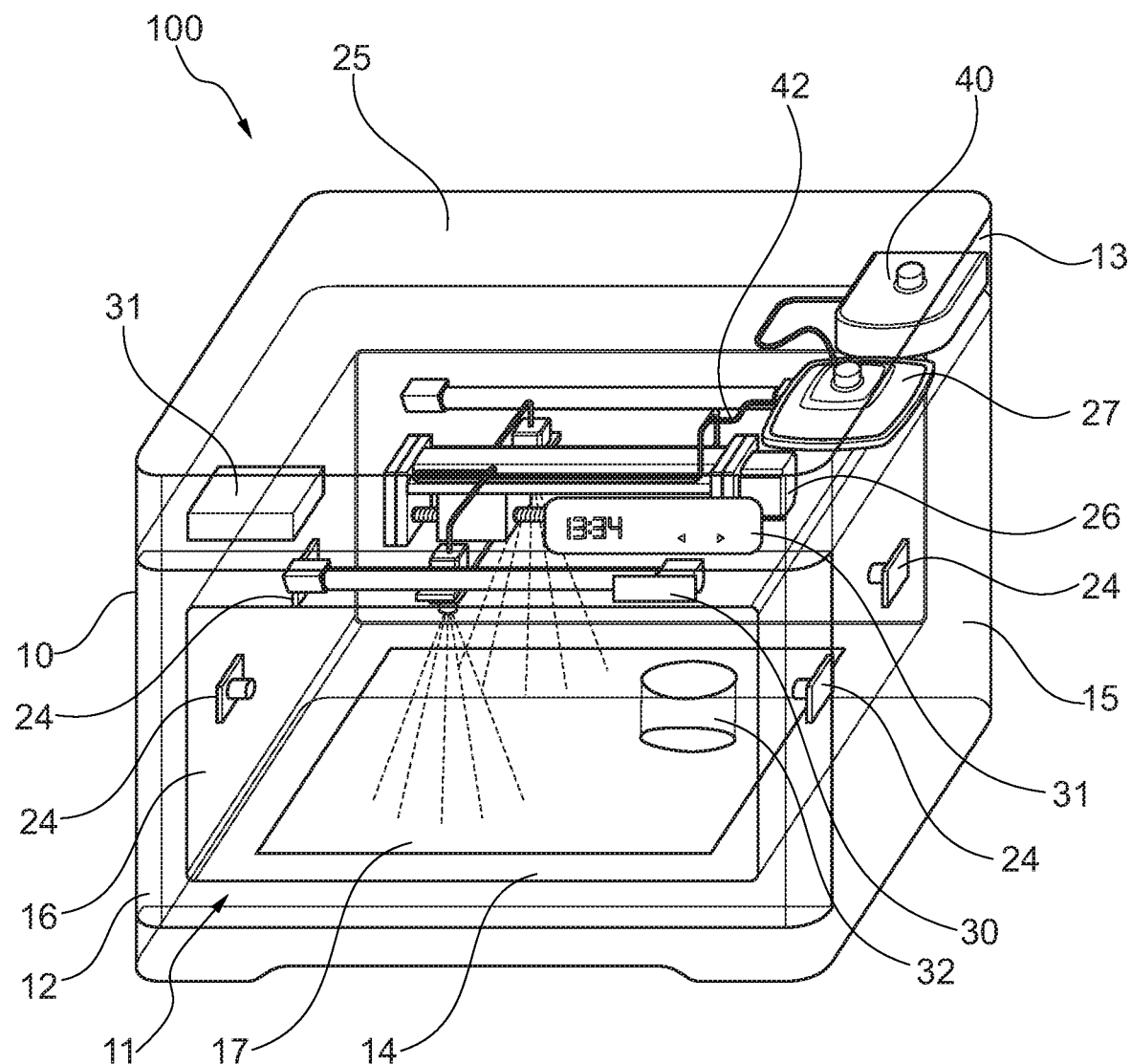
FIG. 3 is a perspective view of the sanitizing and disinfecting device showing the main components of the device according to one embodiment of the present invention.

According to FIGS. 1 to 3 a sanitizing and disinfecting device 100 is disclosed. The device has two main components: a) a chamber 10 containing UV-C lamps and a system to facilitate spray coating application, and b) an antimicrobial liquid coating that is UV curable. The chamber 10 is made of a group of material consisting of a polymer, a metal, a plastic which does not allow UV light to pass through.

The chamber 10 has a top portion 13, a bottom portion 14, a right side wall 15, a left side wall 16 and an opening in the front 11 defining a door 12 for the placement of an object 50 to be disinfected inside the device 100. In one embodiment the chamber 10 is rectangular and is configured to accommodate tablet computers, cellphones, and keyboards. A handle 32 on the front door 12 is provided for opening and closing the door.

The inside walls of the chamber are highly reflective and are made of materials including but not limited to UV fused silica, $CaF_2$, $MgF_2$, $BaF_2$, quartz, sapphire, Teflon, polydimethylsiloxane, TPX® or polymethylpentene (PMP).

Figure 4:
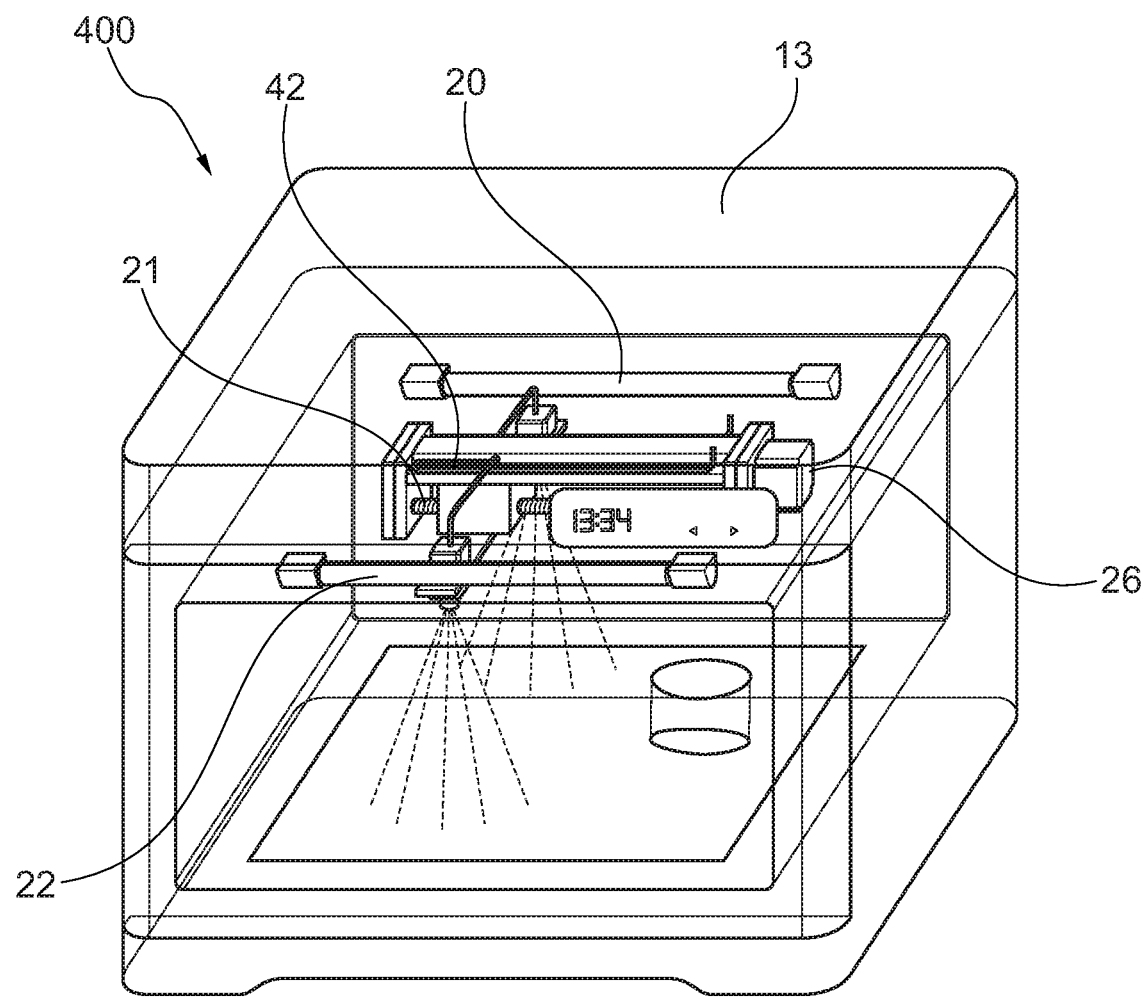
FIG. 4 is a perspective view of the top wall of the device showing the UV-C lamps and the antimicrobial coating system of the device according to one embodiment of the present invention.

According to FIGS. 3 and 4 the device 100 comprises a first UV-C lamp 20 and a second UV-C lamp 22 mounted on to the top wall 13 inside the chamber in a predefined distance and parallel to each other. The first UV light source and the second UV light source can be the same or can be selected from different germicidal UV light sources.

The device further comprises of an antimicrobial coating system comprising a spraying system 23 mounted on the top wall 13 of the chamber. The spraying system 23 comprises one or more nozzle heads and is moveable on a treaded screen 21 between the UV light sources 20 and 22. A motor 25 is provided to control the movement of the spraying system. The antimicrobial coating system further includes components to deliver the antimicrobial material from the tank 27 into the channels 42 and direct it into the spraying system 23.

A compressor 40 having an air intake opening 41 is provided for distribution of the liquid antimicrobial material. Therefore, the coating material distributes evenly, since the air flows in an annular supply channel and surrounds the stream of coating material. The compressor 40 makes the flow of the material into the channels 42 and to the nozzle 23. In one embodiment a shut-off valve is installed for controlling the supply of the coating material into the channel that is not represented in the figures.

The antimicrobial UV curable coating is formulated by mixing a urethane acrylate, a photoinitiator, a reactive diluent for adhesion promoting (monofunctional acrylate), an acrylate-based reactive diluent for lowering the surface tension, and a long-chain alkyl acrylate for providing hydrophobic property. The coating can be hydrophilic, water repellent (hydrophobic), highly water repellent (superhydrophobic), oil repellent (oleophobic) or omniphobic.

The coating material forms a uniform layer with a strong adhesive properties on the object which provides a long lasting protection on the surface of the device. The antimicrobial material is filled into the tank 27 provided in the compartment 25. The tank 27 is connected to the nozzle through channels 42.

The layer thickness itself is governed by the amount of material, the material viscosity and the intensity of the air supplied. The control system controls the amount of the coating material, therefore, is suitable for coating with any coating material that can be applied to the surface of the devices. The pressure of the air in the compressor is increased or decreased to control the amount of coating. In a preferred embodiment the nozzle has a shut-off valve, preferably a ball valve to control the amount of the coating material. The antimicrobial coating material is guided into the channels 42 from the tank 27 that is under air pressure by the air compressor 40. The coating material leaves in the form of a spray and forms a layer of coating on the object. By appropriate setting of the pressure and the amount of air, the amount of coating can be set.

Figure 5A:
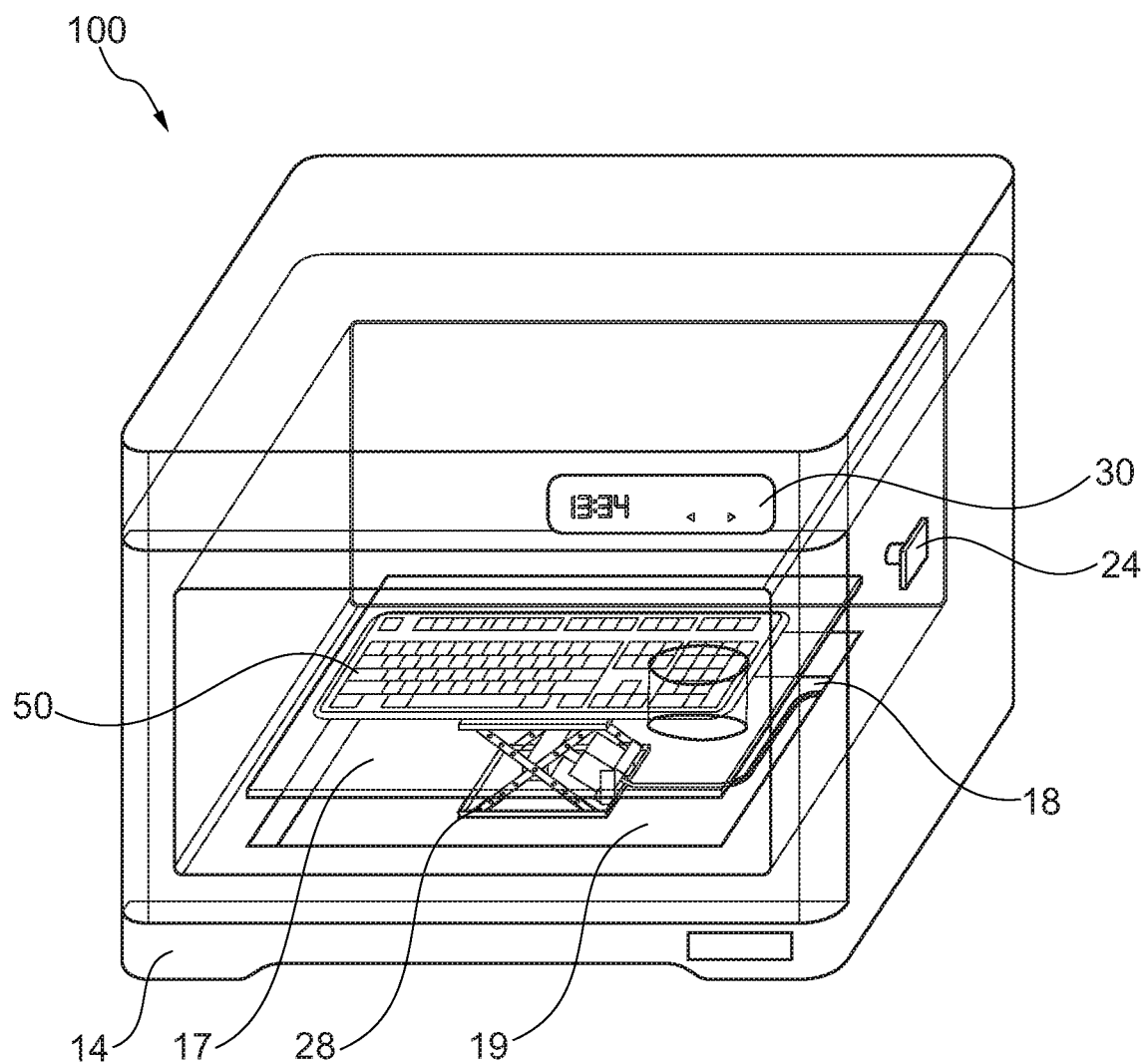
FIG. 5A is a perspective view of the bottom of the device showing elevating platform of the device according to one embodiment of the present invention.
Figure 5B:
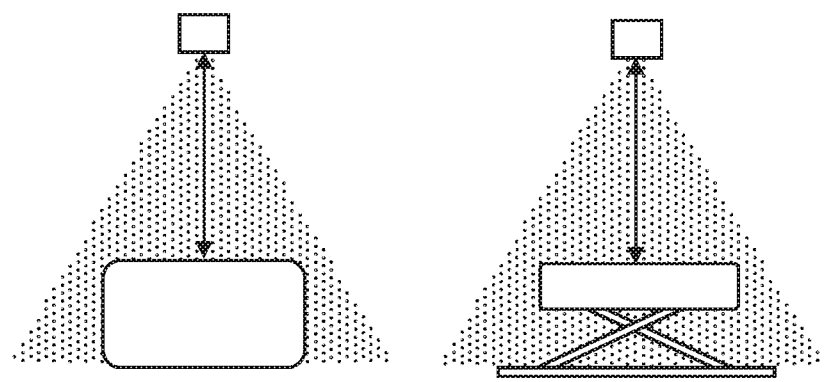
FIG. 5B is a side view of the bottom of the device showing elevating platform of the device according to one embodiment of the present invention.

Referring to FIGS. 3, 5A and 5B, an elevating platform 17 is mounted on the bottom 14 of the chamber, which has a motor 18 to raise and lower the platform 17, thereby positioning any object that is on the platform 17 for disinfection in an appropriate distance to the spray nozzles and the UV-C lamps 20 and 22. Plurality of positioning laser sensors 24 on the right wall 15 and the left wall 16 control the appropriate height of the platform 17. The height of the platform 17 is changed based on the distance between the spray nozzle and the object surface. The platform is adjusted to a predetermined distance, according to the dimension of the object, to avoid the splashes of the coating material and prevent of dripping effectively.

In one embodiment of the present invention, a plurality of laser sensors is attached to different portion of the side walls of the sanitizing and disinfecting device to identify the height of an object or a height of a portion of an object. By the information collected from the laser sensors, a topography of the surface can be identified so the area can be divided to several sub-areas. Each sub-area with similar height is elevated to receive a proper coating.

Proper positioning of the item under the spray is crucial for the coating thickness on the item. The spray diverges downstream of the nozzle and therefore, the mass of the spray is spread over a larger area. Therefore, if the item is farther away from the nozzle, it received less mass per unit area in a set time, and the coating is thinner. On the other hand, if the item is closer to the spray nozzle, it will receive more mass per unit area in the same time period. The distance of the item to the spray nozzle is adjusted to provide a uniform coating or a known thickness on all items.

The bottom of the chamber 14 has an opening 19 formed therethrough sized to accommodate various parts to raise and lower the platform 17 vertically. Various well known drive systems in the art can be installed to raise and lower the platform including but not limited to a drive carriage or a jack 28. The movement of the platform 17 is enhanced by the motor 18 which is installed in the opening 19 and is controlled by the control system 31 to raise the platform to a predefined height.

A control system to control a set of device functions and to elevate the object to have a minimum distance between the spray nozzle and the top surface of the object to assure that spray provides a proper coating, and at least a sensor in communication with the control system to measure and communicate the distance between the top surface of the object and the spray nozzle.

The device has a control system 31 comprising an electric circuit board for controlling the functionalities of the device 100. The control system 31 controls the following functionalities of the device 100:

controlling the movement of the platform 17 in respect to the UV-C lights 20 and 22 and the nozzle 23 by controlling the sensors 24 and the motor 18;
controlling the activation and deactivation of the first and second UV-C light sources 20 and 22 based on a pre-determined time;
controlling activation and deactivation of the spraying system 23 by controlling the motor 26 based on a pre-determined time;
controlling the flow of the liquid antibacterial material inside the channel 42 by controlling the compressor 40;
controlling the LED display 30 for indicating a status of the sterilization cycle and showing the beginning or completion of a sterilization cycle;
controlling and ensuring the door 12 is locked after placing the object inside the chamber 10 for safety reasons;
generating a report on time and duration of a sanitization cycle;
warning when the UV light sources 20 and 22 require replacement, and
warning when the antimicrobial material in the tank 27 requires to be filled.

The control system 31 further comprises a LED touch-screen interface 30 for selecting the functionalities of the device. The LED interface 30 further has an emergency shutdown button, an on/off switch, a status indicator light or an alarm light. An indicator light turns on to let the user know that the system is ready to use after the object is at the right distance from the UV-lamps. When the user presses the on-switch on the display 30, the UV-C lamps turn on for a pre-programmed amount of time.

A compartment 25 on top of the device 100 receive various components of the device 100, such as the compressor 40, the antimicrobial coating tank 27 and the control system 31.

This device 100 uses stationary UV-C lamps and controls the exposure time. In addition, the device 100 controls the position of the item from the UV lamp to have adequate exposure for sanitization. Finally, the device 100 automatically applies a very thin layer of antimicrobial coating that provides a long-term antimicrobial solution.

The object 50 may be a hand-held device, such as cellphones, tablet computers, keyboards and mouse or other devices which are exposed to the contamination. The coating will further provide an additional layer of protection from scratch, dust, smudge and weather as the coating will be hydrophobic (anti-wetting) in nature. The coating itself will not change the aesthetic or functions of the objects.

Figure 6:
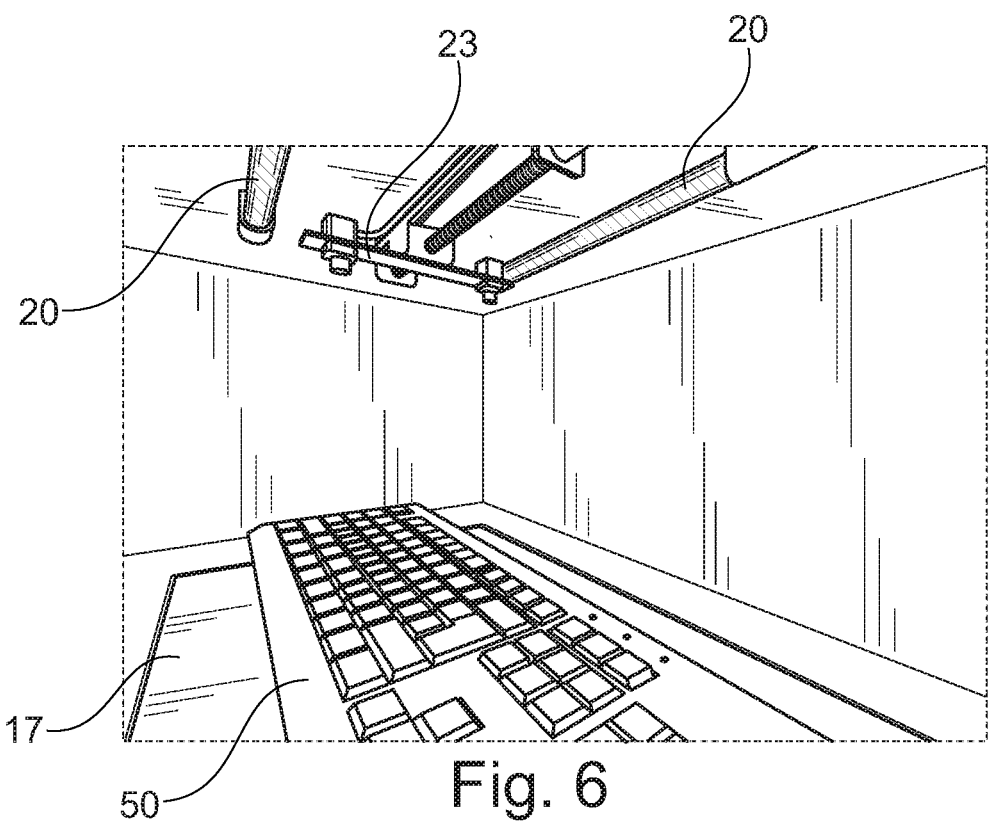
FIG. 6 is a perspective view of the sanitizing and disinfecting environment of the device showing the first step of the sanitizing session with UV-C lights emitted on the object for a pre-programmed amount of time.
Figure 7:
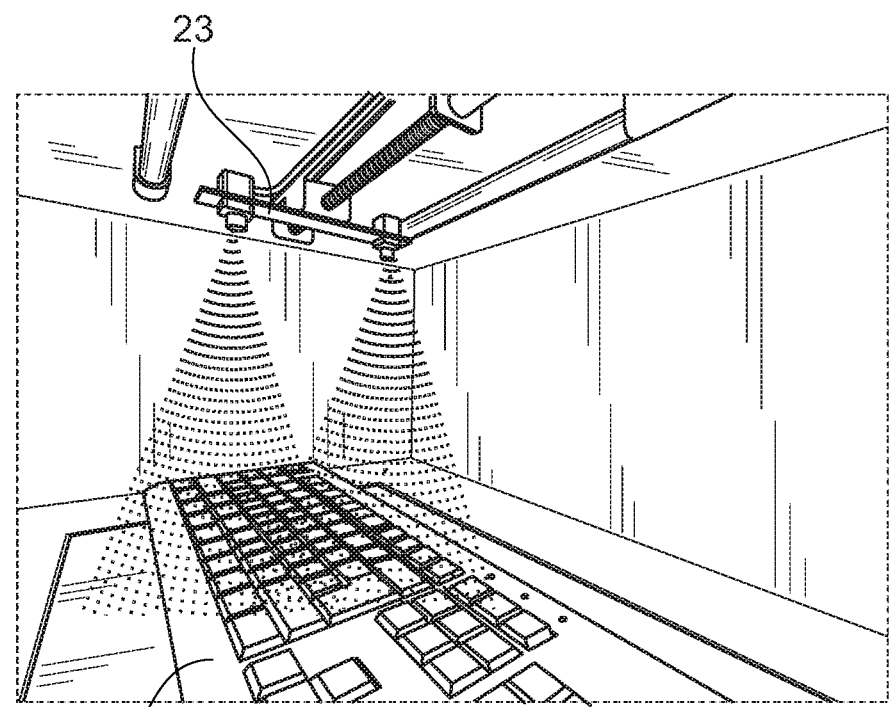
FIG. 7 is a perspective view of the sanitizing and disinfecting environment of the device showing the second step of the sanitizing and disinfecting process with spraying a predetermined amount of the antibacterial liquid coating over the object.
Figure 8:
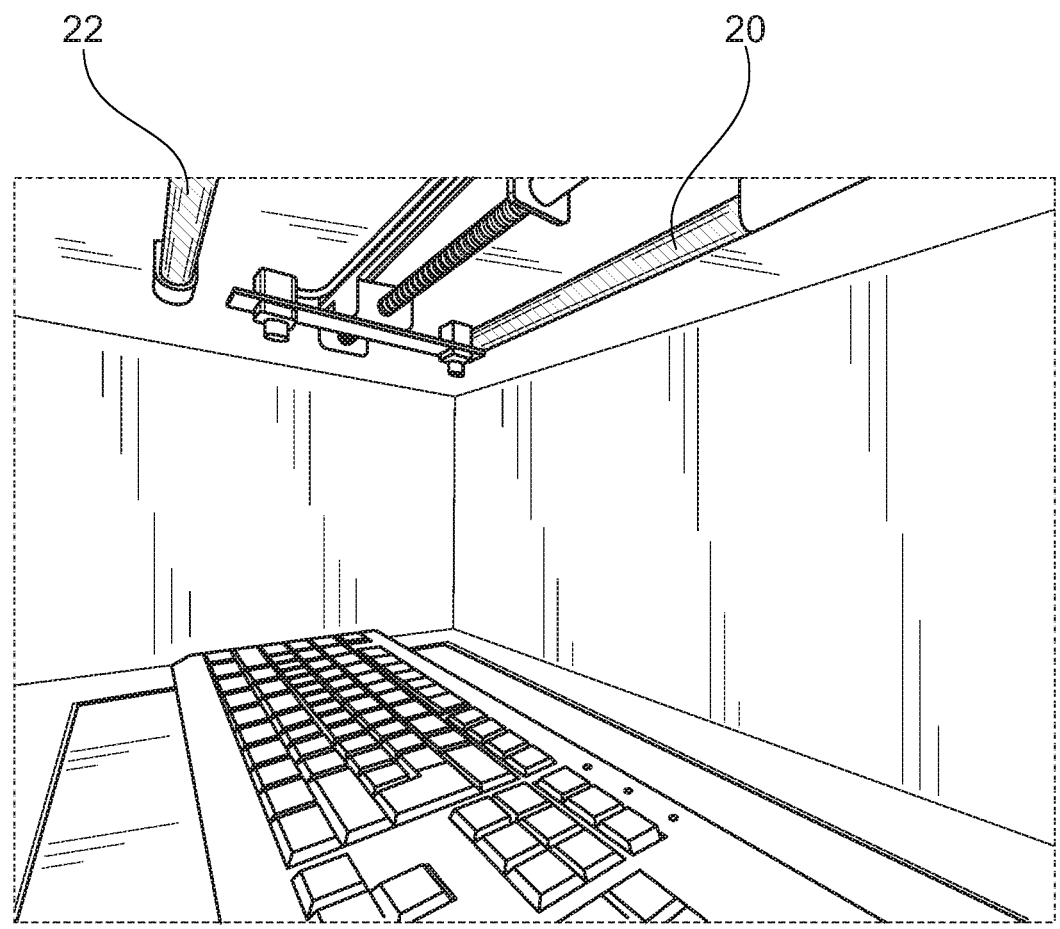
FIG. 8 is a perspective view of the sanitizing and disinfecting environment of the device showing the third step of sanitizing and disinfecting process with the UV-C lamps turn on for a pre-defined time to cure the antimicrobial coating on the object.

FIGS. 6, 7 and 8 show the three steps procedure of the sanitization and disinfection according to the present invention. After positioning the object 50 on the platform 17 the control system 31 ensure that the door 12 is locked after placing the item inside the chamber. The electric control system also controls that the platform motor 18 activates and elevates the platform 17 to position the item 50 at an appropriate height by using positioning lasers 24.

A warning light on the display 30 turns on, letting the user know that the system is ready to use after the object 50 is at the right distance from the UV-C lights. When the user presses the on-switch, the UV-C lights 20 and 22 turn on for a pre-programmed amount of time. After the initial sanitizing session, the UV-C lamps turn off automatically, and the spraying system gets activated. The nozzle 23 moves back and force on the threaded screen 21 and sprays a thin layer of the antimicrobial liquid coating over the object 50. Then, the UV-C lamps 20 and 22 turn on for a pre-defined time to cure the coating on the object. When the whole operation is completed, the system lets the user know by turning on another LED light. During the operation, if the user accidentally opens the door, the system automatically shuts down everything, including the UV-C lamps and the spray system.

The first UV light source and the second UV light source can be the same or can be selected from different germicidal UV light sources. and can be independently selected from the group consisting of a low pressure mercury lamp, a medium pressure mercury lamp, a high pressure mercury lamp, an ultra-high pressure mercury lamp, a low pressure short arc xenon lamp, a medium pressure short arc xenon lamp, a high pressure short arc xenon lamp, an ultra-high pressure short arc xenon lamp, a low pressure long arc xenon lamp, a medium pressure long arc xenon lamp, a high pressure long arc xenon lamp, an ultra-high pressure long arc xenon lamp, a low pressure metal halide lamp, a medium pressure metal halide lamp, a high pressure metal halide lamp, an ultra-high pressure metal halide lamp, a tungsten halogen lamp, a quartz halogen lamp, a quartz iodine lamp, a sodium lamp, and an incandescent lamp. The first UV lamp and the second UV lamp can further be selected from the group consisting of low-pressure UV lamp, a medium pressure UV lamp, a high pressure UV lamp, and an ultra-high-pressure lamp.

The positioning system and exposure time control ensure that the object receives an optimal level of UV-C light, which is required to kill the microbes and sanitize the object. The safety lock system ensures that the UV-C light are on when the door is open to protect the user from the harmful effect of UV light. The antimicrobial coating adds long-term antimicrobial functionality.

In another embodiment the spray coating can be applied manually on the object and then placed in the device to cure with the UV-C lamp.

Figure 9A:
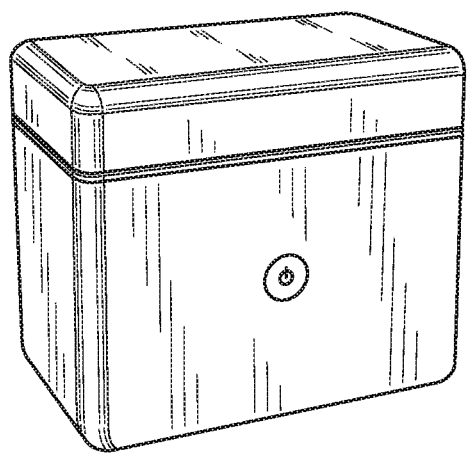
FIG. 9A is a perspective view of another embodiment of the present invention.
Figure 9B:
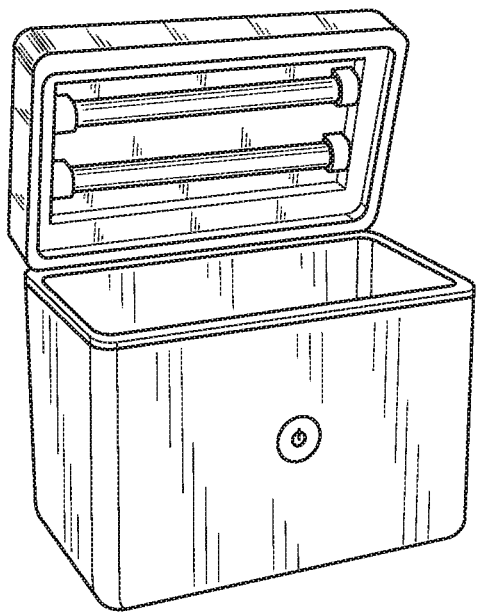
FIG. 9B is a perspective view of another embodiment of the present invention.

In another embodiment, as reflected in FIGS. 9A and 9B, the device further has the two main components: a) a chamber containing UV-C lamps and necessary parts to facilitate spray coating application, and b) an antimicrobial liquid coating that is UV curable. The chamber is rectangular and has enough space to accommodate tablet computers, cellphones, and keyboards. A lid on top allows placing an item that requires sanitization for the household items. The inside wall of the chamber is highly reflective. UV-C lamps are placed at the ceiling of the chamber.

An electric circuit ensures that the door is locked after placing the item inside the chamber, and a LED turns on to confirm it. When the user presses the on-switch, the UV-C lamps turn on for a pre-programmed amount of time. After the initial sanitizing session, the UV-C lamps turn off automatically. The customers manually spray the coating on the sanitized surface and then, the UV-C lamps turn on for a pre-defined time to cure the coating on the item. When the whole operation is completed, the system lets the user know by turning on another LED. During the operation, if the user accidentally opens the door, the system automatically shuts down everything, including the UV-C lamps and the spray system.

The UV-C light sources each produce a UV light intensity within a range of between 1,300 $\mu Ws/cm^2$ to 440,000 $\mu Ws/cm^2$.

In another embodiment of the present invention, the device equipped with a control panel to choose a pre-programmed process for coating and curing for sanitizing session. A user can choose the pre-programmed process based on their needs.

The UV lamps have a specific lifespan, and they should be replaced after around 9000 hours of operation or every 12 months. The present invention can measure and record the times that UV lamps are in use and after a specific time of using or sanitization cycles, remind the users to change or replace the UV lamps in order to keep the maximum efficiency.

The foregoing is considered as illustrative only of the principles of the invention.

Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

What is claimed is:

1. A sanitizing and disinfecting device to sanitize an object, the device comprising:
   a) a chamber comprising a top portion, a bottom portion having a movable platform to receive the object, a right side wall and a left side wall, and a front door for placement of the object onto the movable platform;
   b) a first and a second UV lights mounted on the top portion of the chamber;
   c) an antimicrobial spray coating system having one or more spray nozzles, and mounted on the top portion of the chamber to spay an antimicrobial UV curable material on a top surface of the object;
   d) a self-elevating system attached to a bottom side of the movable platform to elevate the object;
   e) a control system to control a set of device functions and to elevate the object to a predefined distance between the one or more spray nozzles and the top surface of the object to provide a proper coating, and
   f) at least a sensor in communication with the control system to measure and communicate a distance between the top surface of the object and the one or more spray nozzles,
   whereby the sanitizing and disinfecting device provides a thin layer of the UV curable antimicrobial material on the top surface of the object for a long-lasting sanitizing effect.

2. The device according to claim 1, wherein the antimicrobial spray coating system comprising;
   a) a traverse mechanism attached to the top portion of the chamber;
   b) the one or more spray nozzles attached to the traverse mechanism;
   c) a fluid supply system comprising a storage container to store the UV curable antimicrobial material, and
   d) a compressor for distribution of the UV curable antimicrobial material into the one or more spray nozzles.

3. The device according to claim 1, wherein the set of device functions controlled by the control system are selected from the group consisting of:
   a) controlling movement of the self-elevating system with respect to the first and the second UV lights and the one or more spray nozzles;
   b) controlling activation and deactivation of the first and the second UV lights based on a pre-determined time;
   c) controlling activation and deactivation of the one or more spray nozzles;
   d) controlling an LED display for indicating a status of a sterilization cycle and showing start or completion of the sterilization cycle;
   e) controlling and ensuring the front door is locked after placing the object inside the chamber for safety reasons;
   f) generating a report on a time duration of the sanitization cycle;
   g) generating a warning message when the first and the second UV lights require replacement, and
   h) generating a second warning message when the antimicrobial UV curable material in the storage container requires to be re-filled.

4. The device according to claim 1, wherein the first and the second UV lights are selected from the group consisting of low-pressure UV lamp, a medium pressure UV lamp, a high-pressure UV lamp, and an ultra high-pressure lamp.

5. The device according to claim 1, wherein the first and the second UV lights are UV-C lights source.

6. The device according to claim 1, wherein the control system comprising of a control box comprising an emergency shutdown button, an on/off switch, a status indicator light or an alarm light.

7. The device according to claim 1, wherein the object for sterilizing and sanitizing is selected from the group consisting of a hand-held device, a cellphone, a tablet computer, a keyboard and a mouse, or other devices which are exposed to the contamination.

8. The device according to claim 1, wherein the antimicrobial UV curable material is formulated by mixing a urethane acrylate, a photo initiator, a reactive diluent for adhesion promoting (monofunctional acrylate), an acrylate-based reactive diluent for lowering the surface tension, and a long-chain alkyl acrylate for providing hydrophobic property, whereby the antimicrobial UV curable material forms a uniform layer on the top surface of the object with a strong adhesive property and a long-lasting protection.

9. The device according to claim 1, wherein the antimicrobial UV curable material is hydrophilic, water repellent (hydrophobic), highly water repellent (super hydrophobic), oil repellent (oleo phobic) or Omni phobic.

* * * * *